United States Patent
Ralph et al.

(10) Patent No.: US 6,758,861 B2
(45) Date of Patent: *Jul. 6, 2004

(54) INTERVERTEBRAL SPACER DEVICE HAVING A WAVE WASHER FORCE RESTORING ELEMENT

(75) Inventors: James D. Ralph, Lehigh Valley, PA (US); Stephen Tatar, Montville, NJ (US); Joseph P. Errico, Kirkland, WA (US)

(73) Assignee: SpineCore, Inc., Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/272,580

(22) Filed: Oct. 16, 2002

(65) Prior Publication Data

US 2003/0040801 A1 Feb. 27, 2003

Related U.S. Application Data

(63) Continuation of application No. 09/906,117, filed on Jul. 16, 2001, now Pat. No. 6,468,310.

(51) Int. Cl.$^7$ .................................................. A61F 2/44
(52) U.S. Cl. ..................................................... 623/17.13
(58) Field of Search ........................ 623/17.11, 17.13, 623/17.14, 17.15, 17.16; 606/61

(56) References Cited

U.S. PATENT DOCUMENTS

| | | | | | |
|---|---|---|---|---|---|
| 4,309,777 | A | * | 1/1982 | Patil | 623/17.13 |
| 5,928,284 | A | * | 7/1999 | Mehdizadeh | 623/17.13 |
| 6,231,609 | B1 | * | 5/2001 | Mehdizadeh | 623/17.11 |
| 6,454,806 | B1 | * | 9/2002 | Cohen et al. | 623/17.15 |
| 6,468,310 | B1 | * | 10/2002 | Ralph et al. | 623/17.13 |
| 6,520,996 | B1 | * | 2/2003 | Manasas et al. | 623/23.5 |
| 6,527,804 | B1 | * | 3/2003 | Gauchet et al. | 623/17.12 |
| 6,527,806 | B2 | * | 3/2003 | Ralph et al. | 623/17.16 |
| 6,579,320 | B1 | * | 6/2003 | Gauchet et al. | 623/17.15 |
| 6,723,127 | B2 | * | 4/2004 | Ralph et al. | 623/17.13 |
| 2002/0128714 | A1 | * | 9/2002 | Manasas et al. | 623/17.15 |

* cited by examiner

Primary Examiner—Eduardo C. Robert
(74) Attorney, Agent, or Firm—Joseph P. Errico, Esq.; Timothy J. Bortree, Esq.

(57) ABSTRACT

An intervertebral spacer device having a pair of opposing plates for seating against opposing vertebral bone surfaces, separated by at least one force restoring element. The preferred force restoring mechanism is a wave washer. In a first embodiment the wave washer is ring-shaped. In a second embodiment the wave washer is spiral-shaped.

19 Claims, 5 Drawing Sheets

INTERVERTEBRAL SPACER DEVICE HAVING A WAVE WASHER FORCE RESTORING ELEMENT

CROSS-REFERENCE TO RELATED APPLICATION

This application is a continuing application of U.S. patent application Ser. No. 09/906,117 (filed Jul. 16, 2001) entitled "Intervertebral Spacer Device Having a Wave Washer Force Restoring Element", now U.S. Pat. No. 6,468,310, which application is hereby incorporated by reference herein in its entirety.

FIELD OF THE INVENTION

This invention relates generally to a spinal implant assembly for implantation into the intervertebral space between adjacent vertebral bones to simultaneously provide stabilization and continued flexibility and proper anatomical motion, and more specifically to such a device which utilizes a wave washer as a force restoring element.

BACKGROUND OF THE INVENTION

The bones and connective tissue of an adult human spinal column consists of more than 20 discrete bones coupled sequentially to one another by a tri-joint complex which consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes which can result in spinal pathologies for which surgical intervention may be necessary. A variety of systems have been disclosed in the art which achieve immobilization and/or fusion of adjacent bones by implanting artificial assemblies in or on the spinal column. The region of the back which needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 1 and 2, in which a side perspective view of an intervertebral body cage and an anterior perspective view of a post implantation spinal column are shown, respectively, a more complete description of these devices of the prior art is herein provided. These cages 10 generally comprise tubular metal body 12 having an external surface threading 14. They are inserted transverse to the axis of the spine 16, into preformed cylindrical holes at the junction of adjacent vertebral bodies (in FIG. 2 the pair of cages 10 are inserted between the fifth lumbar vertebra (L5) and the top of the sacrum (S1). Two cages 10 are generally inserted side by side with the external threading 14 tapping into the lower surface of the vertebral bone above (L5), and the upper surface of the vertebral bone (S1) below. The cages 10 include holes 18 through which the adjacent bones are to grow. Additional material, for example bone graft materials, may be inserted into the hollow interior 20 of the cage 10 to incite or accelerate the growth of the bone into the cage. End caps (not shown) are often utilized to hold the bone graft material within the cage 10.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which nearly completely mimics the biomechanical action of the natural disc cartilage, thereby permitting continued normal motion and stress distribution.

It is, therefore, an object of the present invention to provide a new and novel intervertebral spacer which stabilizes the spine without promoting a bone fusion across the intervertebral space.

It is further an object of the present invention to provide an implant device which stabilizes the spine while still permitting normal motion.

It is further an object of the present invention to provide a device for implantation into the intervertebral space which does not promote the abnormal distribution of biomechanical stresses on the patient's spine.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a flexible intervertebral spacer device comprising a pair of spaced apart base plates, arranged in a substantially parallel planar alignment (or slightly offset relative to one another in accordance with proper lordotic angulation) and coupled to one another by means of a spring mechanism. In particular, this spring mechanism provides a strong restoring force when a compressive load is applied to the plates, and may also permit limited rotation of the two plates relative to one another. While there are a wide variety of embodiments contemplated, two embodiment families are described herein as representative of preferred types. Each of these embodiments includes a wave washer utilized as its force restoring element.

More particularly, with respect to the base plates, which are similar in all embodiments, as the assembly is to be positioned between the facing surfaces of adjacent vertebral bodies, and as such need to have substantially flat external surfaces which seat against the opposing bone surfaces. Inasmuch as these bone surfaces are often concave, it is anticipated that the opposing plates may be convex in accordance with the average topology of the spinal anatomy. In addition, the plates are to mate with the bone surfaces in such a way as to not rotate relative thereto. (The plates rotate relative to one another, but not with respect to the bone surfaces to which they are each in contact with.) In order to prevent rotation of a plate relative to the bone, the upper and lower plates may each include outwardly directed spikes which penetrate the bone surface and mechanically hold the plates in place. Alternatively, the base plates may be coupleable to other securing means for holding the present invention in place.

It is further anticipated that the plates may include a porous coating into which the bone of the vertebral body can grow. (Note that this limited fusion of the bone to the base plate does not extend across the intervertebral space.)

Between the base plates, on the exterior of the device, there is included a circumferential wall which is resilient and which simply prevents vessels and tissues from growing into the interior of the device. This resilient wall may comprise a porous fabric or a semi-impermiable elastomeric material, and serves a similar purpose to the naturally occurring annulus material which surrounds the cartilage of the intervertebral disc, which the present invention is designed to replace when conditions warrant. Suitable tissue compatible materials meeting the simple mechanical requirements of flexibility and durability are prevalent in a number of medical fields including cardiovascular medicine, wherein such materials are utilized for venous and arterial wall repair, or for use with artificial valve replacements. Alternatively, suitable plastic materials are utilized in the surgical repair of gross damage to muscles and organs. Still further materials which could be utilized herein may be found in the field of orthopaedic in conjunction with ligament and tendon repair. It is anticipated that future developments in this area will produce materials which are compatible for use with this invention, the breadth of which shall not be limited by the choice of such a material.

As introduced above, the internal structure of the present invention comprises a force restoring member, which provides a restoring force when compressed. More particularly, it is desirable that the restoring forces be directed outward against the opposing plates, when a compressive load is applied to the plates.

In addition, in certain select embodiments, it is necessary that the restoring force providing subassembly not substantially interfere with the rotation of the opposing plates relative to one another. In the first embodiment, the force restoring subassembly does not interfere with the rotation of the plates. In the second preferred embodiment, the spring subassembly substantially inhibits any rotation of the plates relative to one another. As further mentioned above, the force restoring member comprises at least one wave washer.

More particularly with respect to the first embodiment, in which the restoring force providing subassembly does not interfere with the rotation of the plates, the restoring force providing subassembly comprises a single wave washers.

Wave washers resemble simple round washers which comprise a flat round ring, except that while maintaining a constant curvature of radius in the plane normally defined by the washer, the washer rises and falls in a wave-like around its circumference. Stated alternatively, a standard washer is a relatively planar ring-shaped object, confined to the x-y plane. The wave washer is ring-shaped object which undulates in the z-axis around its edge. The restoring force of a wave washer is proportional to the elastic properties of the material. In addition, the magnitude of the compressive load support and the restoring force provided by the wave washer may be modified by altering the thickness of the material in its radial extent, or in its z-axis, or, alternatively, by providing a radial slot in it. (For the purposes of this description, the top and the bottom of a wave washer shall be defined as the planes defined by the highest and lowest points of the circumferential undulations, respectively.)

As a compressive load is applied by a pair of plates against the top and bottom of a wave washer, the forces are directed against the arches of the undulating wave, and are also translated into a hoop stress which tends to radially expand the washer in its x-y plane. This force of deflection against the arches, and the hoop stress in the radial direction, are counterbalanced by the material strength of the washer. The strain of the material causes a deflection in the height of the washer and a slight radial expansion. (It shall be understood that in the embodiments in which the washer includes a radial slot, and in which the washer is constrained against radial expansion, for example by guard walls of the corresponding base plates, the deflection of the arches is not translated into a hoop stress, but rather into a circumferential deflection and closure of the slot.) Stated equivalently, a wave washer responds to a compressive load by deflecting compressively in z-axis, and either radially or circumferentially. The restoring force which is therefore proportional to the elastic modulus. With a slot formed in the washer, it expands and restores itself far more elastically than a continuous ring washer.

In general, the wave washer is one of the strongest configurations for a spring, and is highly suitable for use as a restoring force providing subassembly for use in an intervertebral spacer element which must endure considerable cyclical loading in an active human adult. In the first embodiment of the present invention, the ring-shaped wave washer is secured by a series of pins which extend upwardly and outwardly from one of the inner surfaces of one of the base plates. A compressive load applied to the base plates causes the corresponding compression of the washer, which in turn causes a restoring force to be applied to the base plates. The washer deflects appropriately under the load, only to spring back into its undeflected shape upon the unloading of the spring.

It shall be understood that the securing pins, as well as the exterior circumferential elastomeric material place constraints on the extent to which one base plate may rotate relative to the other. In this way the base plates may rotate relative to one another while maintaining a constant resilient capacity relative to the adjacent bone.

In a second embodiment of the present invention, a single modified wave washer, which is spiral-shaped, as opposed to being ring-shaped. More particularly, instead of the wave washer described in conjunction with the first embodiment, which defines a circumference of 360 degrees (in the solid variant) or less (the slotted variant), the wave washer of the second embodiment sweeps through an angle of 720 degrees or more (depending upon to specific anatomical needs). The undulations of the washer on the z-axis may be such that the arches are aligned, or misaligned. In the variant in which the arches are aligned, securing pins of the type introduced above (which extend upward and radially outward from the interior surface of one of the base plates) may be employed to hold the spiral wave washer in place. The alternative variant may be secured by a simple screw which locks one of the ends of the washer to the base plate.

Finally, inasmuch as the human body has a tendency to produce fibrous tissues in perceived voids, such as may be found within the interior of the present invention, and such fibrous tissues may interfere with the stable and/or predicted functioning of the device, preferred embodiments of the present invention may be filled with a highly resilient elastomeric material. The material itself should be highly biologically inert, and should not substantially interfere with the restoring forces provided by the spring-like mechanisms therein. Suitable materials may include hydrophilic monomers such as are used in contact lenses. Alternative materials include silicone jellies and synthetic collagens such as have been used in cosmetic applications. As with the exterior circumferential wall, which was described above as having a variety of suitable alternative materials, it is anticipated that future research will produce alternatives to the materials described herein, and that the future existence of such materials which may be used in conjunction with the present invention shall not limit the breadth thereof.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
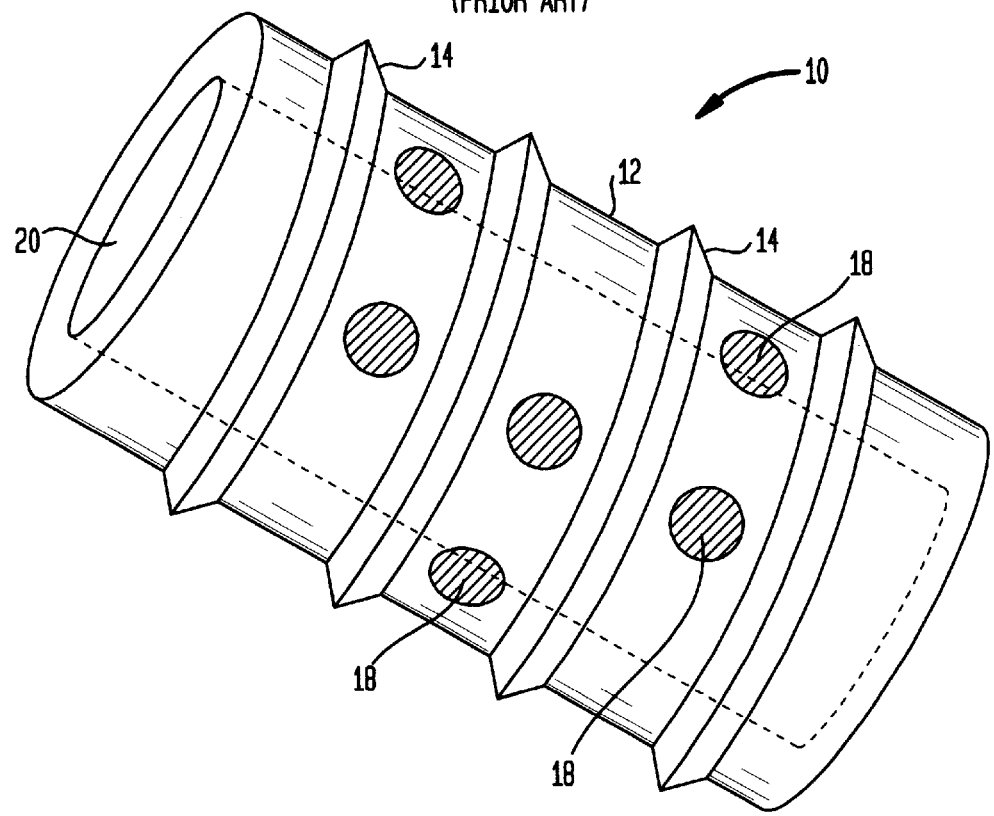
FIG. 1 is a side perspective view of an interbody fusion device of the prior art.
Figure 2:
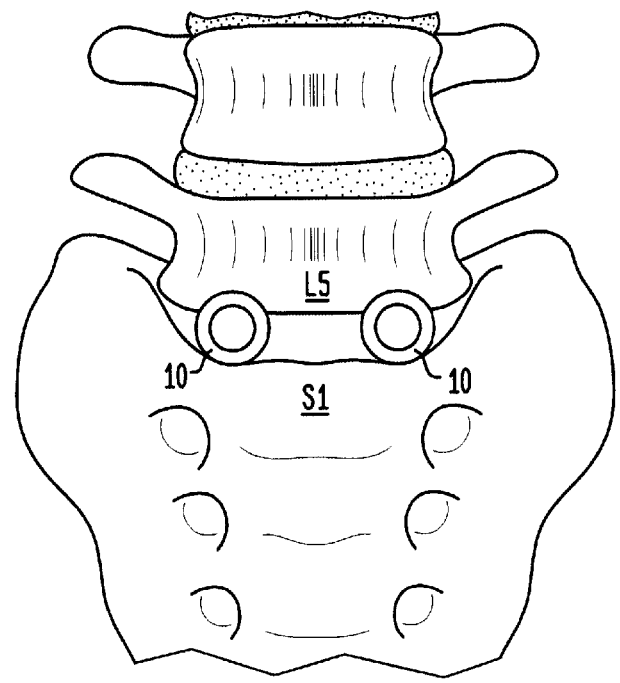
FIG. 2 is a front view of the anterior portion of the lumbo-sacral region of a human spine, into which a pair of interbody fusion devices of the type shown in FIG. 1 have been implanted.
Figure 3A:
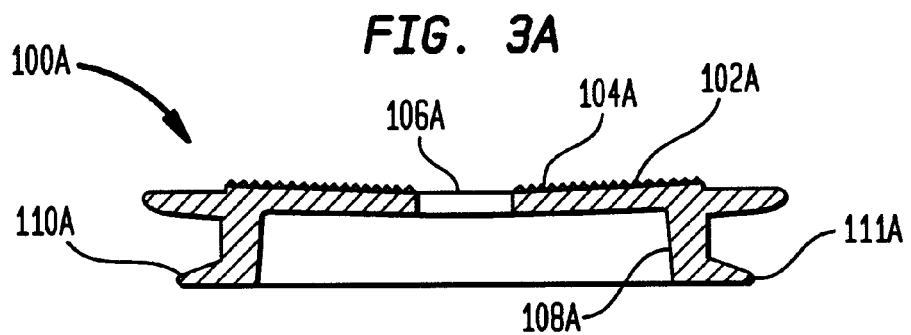
FIGS. 3a and 3b are side cross-section views of the upper and lower opposing plates of the present invention.
Figure 3B:
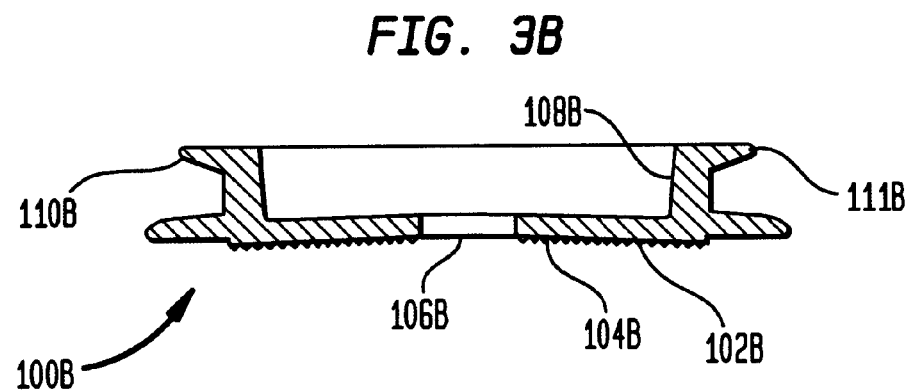

Referring now to FIGS. 3a and 3b, side cross-section views of the top and bottom plate members 100a 100b of a first embodiment of the present invention is shown. More particularly, in this embodiment, the upper and lower plates 100a,100b are substantially identical. As the device is designed to be positioned between the facing surfaces of adjacent vertebral bodies, the plates include substantially flat surface portions 102a,102b which seat against the opposing bone surfaces. In addition, the plates are to mate with the bone surfaces in such a way as to not rotate relative thereto. It is, therefore, preferred that the plates should include a porous coating 104a,104b into which the bone of the vertebral body can grow. (Note that this limited fusion of the bone to the base plate does not extend across the intervertebral space.) An additional threaded hole 106a,106b is provided in each plate such that the interior of the device may be readily accessed if a need should arise.

The plates 100a,100b further include a circumferential flange 108a,108b. The flange 108a,108b may be offset with respect to the front 110a,110b and rear 111a,111b orientation of the overall assembly. More particularly, the offset nature of the flanges 108a,108b is exhibited in the non-symmetric appearance of each flange as it circumscribes the corresponding plate 100a,100b. By this it is meant that the portion of the flange 108a,108b which corresponds to the rear 111a,111b of the device is shorter than the portion corresponding to the front 110a,110b of the device.

Figure 4:
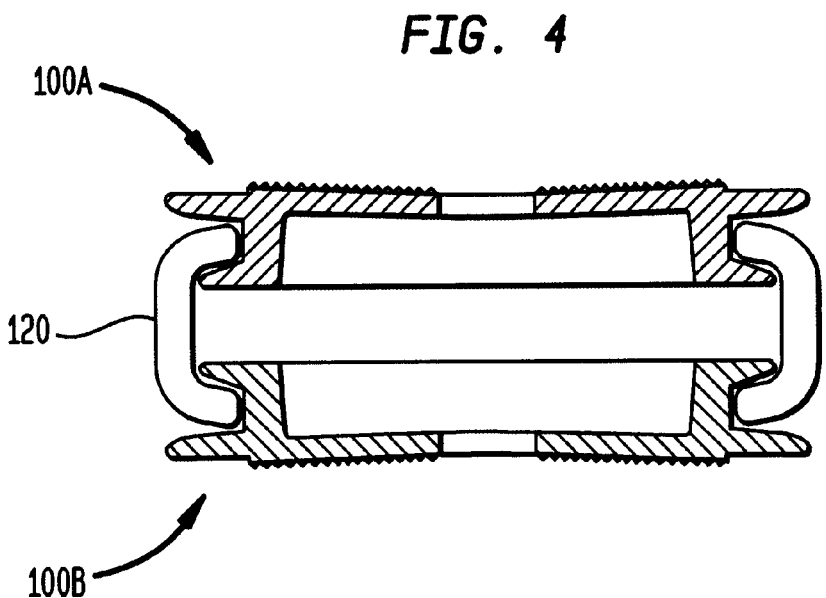
FIG. 4 is a side cross-section view of the opposing plates in association with one another, wherein an exterior skirt is included.

Referring now to FIG. 4, a partially assembled embodiment of the present invention is provided in a side cross-section view, wherein the upper and lower plates 100a,100b illustrated in FIGS. 3a and 3b are joined by means of a circumferential wall 120. More particularly, between the base plates 100a,100b, on the exterior of the device, there is included a circumferential wall 120 which is resilient and which is provided to prevents vessels and tissues from entering within the interior of the device. It is preferred that the resilient wall 120 comprise a porous fabric or a semi-impermiable elastomeric material. The wall 120 is further designs to couple to the flanges 108a,108b of the corresponding plates 100a,100b.

Figure 5A:
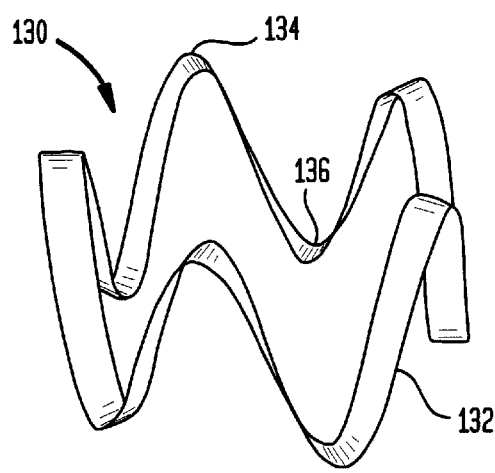
FIG. 5a is a perspective views of solid ring-shaped wave washer of the type which is utilized in conjunction with an embodiment of the present invention.

Referring now to FIG. 5a, one of the possible force restoring elements which may be employed with the present invention is provided in a perspective view. More particularly, the force restoring element comprises a ring-shaped wave washer element 130. In this embodiment, the wave washer 130 is continuous, in that it does not include a radial break. Stated alternatively, the ring-shaped element maintains a circumferentially complete 360 degrees. The wave washer 130 is so named inasmuch as its circumferential conformation includes a rising and falling undulating edge 132, which, while maintaining a constant radius, creates a periodic arches 134 and valleys 136.

The restoring force of a continuous wave washer of the type illustrated in FIG. 5a is proportional to the elastic properties of the material. As a compressive load is applied to the continuous ring-shaped washer, the forces are directed down onto the arches 134 and up against the valleys 136. A significant fraction of these forces are immediately translated into hoop stresses which apply stresses directed toward radially expanding the washer. This hoop stress is also counterbalanced by the material strength of the washer.

Figure 5B:
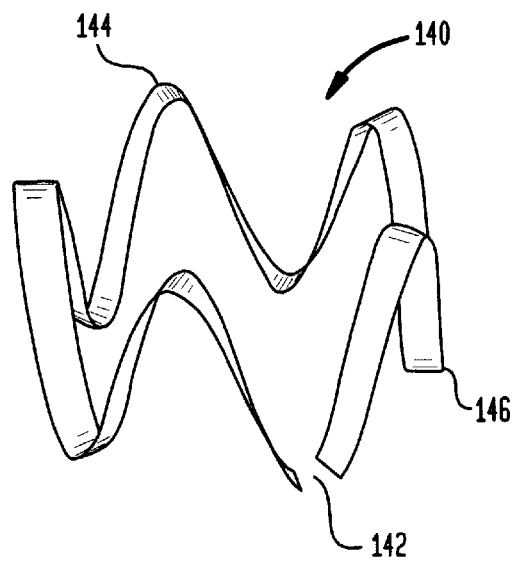
FIG. 5b is a perspective view of a slotted ring-shaped wave washer of the type which is utilized in conjunction with a similar embodiment of the present invention.

FIG. 5b illustrates an alternative ring-shaped wave washer for use with the present invention, which wave washer 140 is radially slotted. This radial slot 142 permits the compressive load which is applied to the washer down onto the arches 144 and up against the valleys 146 to cause the ring to deflect such that the slot 142 closes. Stated equivalently, the difference between the radially slotted washer of FIG. 5b, and the continuous washer of FIG. 5a, is that the continuous washer 130 responds to a compressive load by deflecting radially (with a very high stress to deflection ratio), whereas the radially slotted washer 140 deflects circumferentially, closing the slot 142 (this is characteristic of a much lower stress to deflection ratio).

Figure 5C:
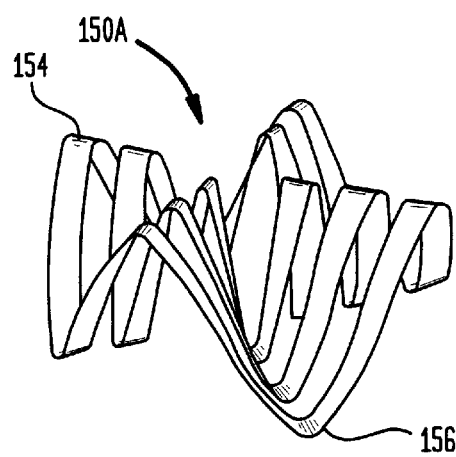
FIGS. 5c and 5d are perspective and top views of a spiral-shaped wave washer of the type which is utilized in conjunction with another embodiment of the present invention.
Figure 5D:
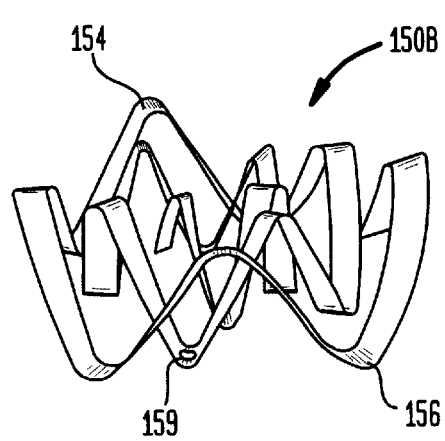

Referring now to FIGS. 5c and 5d, in which perspective views of a two alternative spiral-shaped washers are provided, an alternative embodiment category of the present invention is provided. The spiral-shaped wave washers 150a,150b each comprise a spirally wound band of material (as above, a titanium alloy or stainless steel is preferable, although other suitable surgical materials may be found to function adequately). As with the ring-shaped wave washers 130,140, introduced above, the spirally wound wave washers 150a,150b of this embodiment style includes a series of alternating and undulating arches 154 and valley 156 which extend continuously around the spiral. The wave washer in FIG. 5c shows a washer in which the series of arches and valleys are radially aligned. Alternatively, in FIG. 5d, the arches and valleys are not aligned.

Figure 6A:
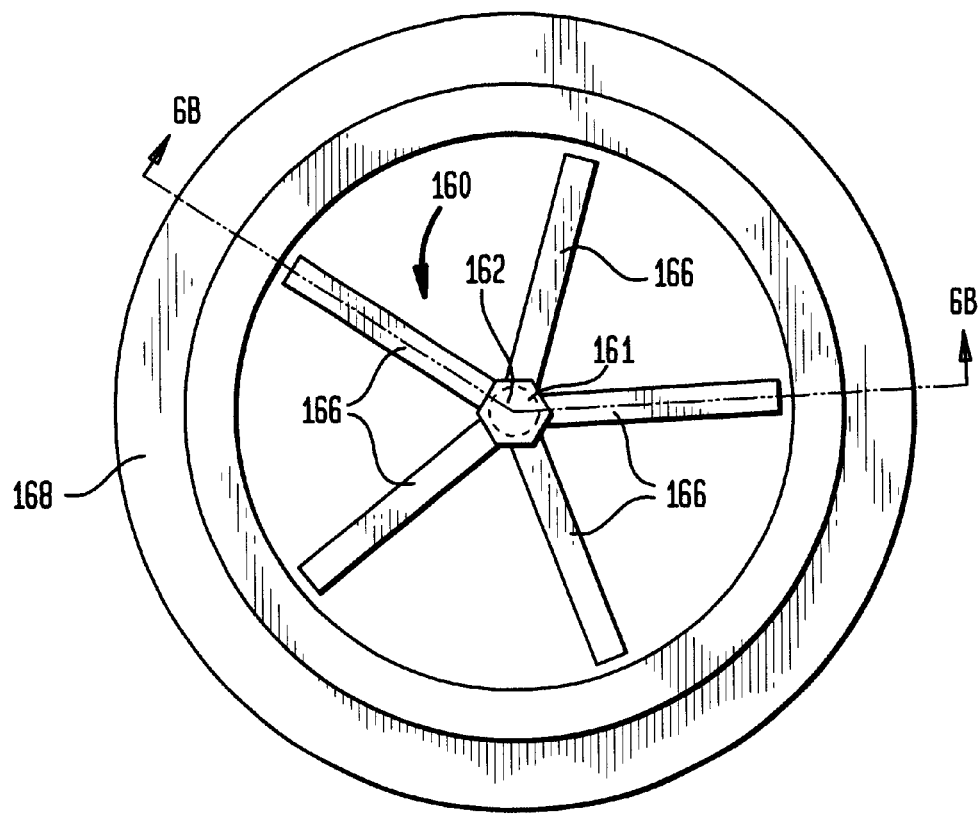
FIGS. 6a and 6b are top and side perspective views of a securing pin assembly and screw for securing a wave washer to a base plate.
Figure 6B:
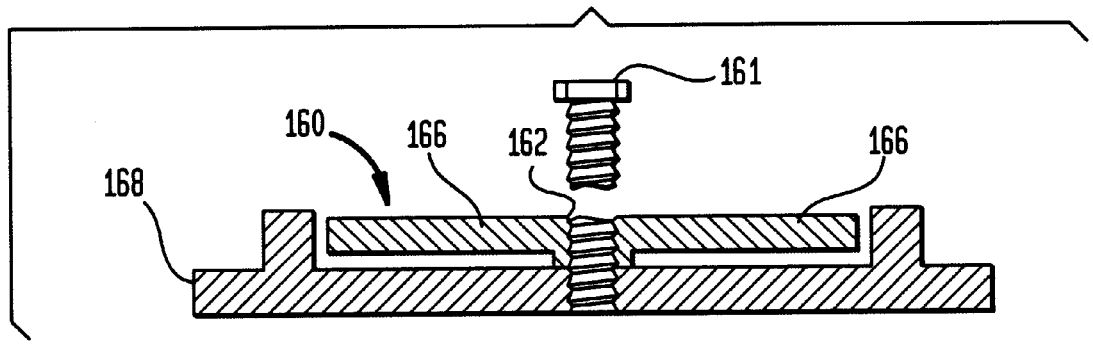

Referring again to FIGS. 3a and 3b and also to FIGS. 6a and 6b, in which a securing pin assembly and screw are provided, a first method of securing a wave washer (either the ring-shaped washers of FIGS. 5a and 5b, or the spiral-shaped washer of FIG. 5c) to a base plate 168 is provided. More particularly, the pin assembly 160 comprises a central hub portion 162 which is flat and includes a threaded hole, having substantially the same diameter and threading as the hole 106a or 106b in the corresponding base plate 100a or 100b. The screw 161 is designed to secure the pin assembly to the base plate. The pin assembly 160 further includes a plurality of radially extending thin shafts 166. These shafts extend outwardly and upwardly from the base plate, aligning themselves in the arches and valleys of the corresponding washer, thereby securing it to the base plate.

Referring now to FIGS. 3a, 3b and 5d, the means for securing the non-aligned spiral-shaped wave washer is now described. At a midpoint (of a valley 156) of the spiral band of the wave washer having non-aligned arches 154 and valleys 156 includes a threaded hole 159 which aligns with the threaded hole 106a or 106b in the base plate to which it is to be secured. The screw 161 shown in FIGS. 6a and 6b secures the washer to the base plate through the aligned holes.

Figure 7:
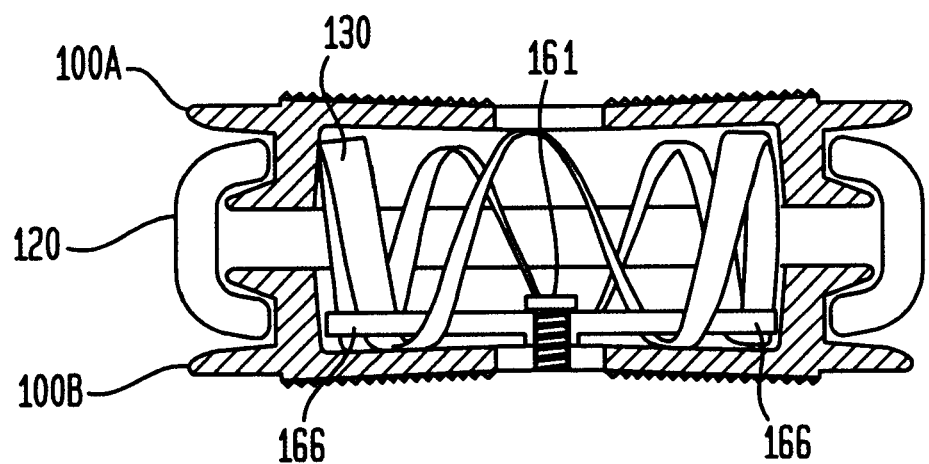
FIG. 7 is a side cross-section view of a first embodiment of the present invention which utilizes ring-shaped wave washer, of the type shown in FIGS. 5a and 5b.

Referring now to FIG. 7, an integrated device embodying the principles of the present invention is provided in a side cross-section view. The base plates 100a,100b are disposed in a spaced apart relationship such that the opposing inner surfaces are approximately parallel and facing one another. A single ring-shaped wave washer 130 or 140 is disposed between the plates, and retained therein by the circumferential flanges 108a,108b. The ring-shaped wave washer 130 or 140 is further constrained against rotational motion by a securing pin assembly 160, and more particularly by the radially extending thin shafts 166. A flexible circumferential skirt 120 is provided around the entirety of the device, such that the tissue of the patient may not grow into, and thereby cause pain, or inhibit the functionality of the device. It shall be understood that a very similar design would accommodate a spiral-shaped wave washer 150a as an alternative to the ring-shaped wave washer, so long as the arches and valleys of the spiral-shaped wave washer are radially aligned, as is shown in FIG. 5c.

Figure 8:
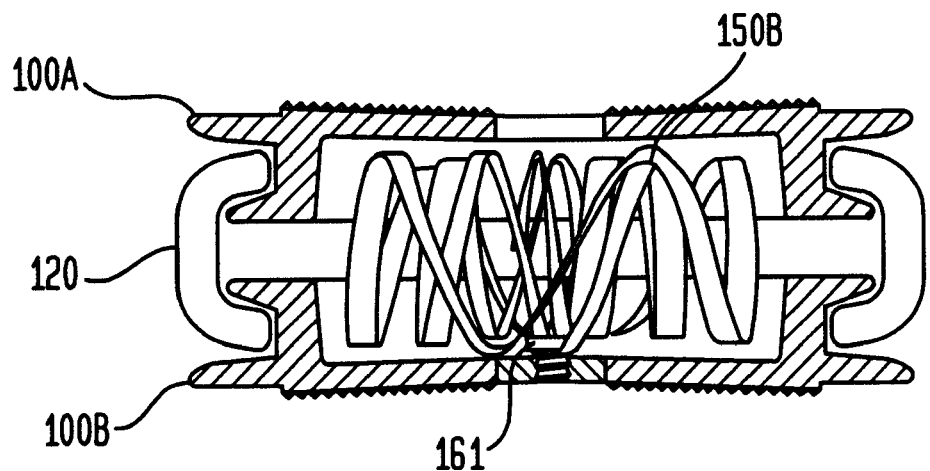
FIG. 8 is a side cross-section view of another embodiment of the present invention which utilizes spiral-shaped wave washer, of the type shown in FIGS. 5c and 5d.

Referring now to FIG. 8, an alternative integrated device embodying the principles of the present invention is provided in a side cross-section view. As with the first embodiment, the base plates 100a,100b are disposed in a spaced apart relationship such that the opposing inner surfaces are approximately parallel and facing one another. In this embodiment, a single spiral-shaped wave washer 150b is disposed between the plates, and retained therein by the circumferential flanges 108a,108b. The spiral-shaped wave washer 150b is further constrained against undesirable translation within the assembly by means of the screw 161 which extends through the central hole 159 of the washer 150b and the hole 106b in the base plate 100b. As in the first embodiment, a flexible circumferential skirt 120 is provided around the entirety of the device, such that the tissue of the patient may not grow into, and thereby cause pain, or inhibit the functionality of the device.

While there have been described and illustrated embodiments of an intervertebral spacer device utilizing a wave washer force restoring element, it will be apparent to those skilled in the art that variations and modifications are possible without deviating from the broad spirit and principle of the present invention. The present invention shall, therefore, be limited only to the full scope of the claims allowable in light of the disclosures made herein.

What is claimed is:

1. An intervertebral spacer device, comprising:
   first and second plates, the plates being disposed in a spaced apart relationship such that one plate surface of the first plate faces one plate surface of the second plate, the facing surfaces being inner surfaces, and alternative faces of each plate being outer surfaces; and
   at toast one restoring force providing element disposed between the inner surfaces of the first and second plates, and disposed such that a compressive load applied to the outer surfaces of the plates is counteracted by the at least one restoring force providing element, the at least one restoring force providing element including at least one wave washer, the at least one wave washer having a longitudinally undulating circumferential extent.

2. The device as set forth in claim 1, wherein the at least one wave washer comprises a ring-shaped wave washer, the ring-shaped wave washer having a longitudinally undulating circumferential extent forming art uninterrupted circular hoop.

3. The device as set forth in claim 1, wherein the at least one wave washer comprises a ring-shaped wave washer, the ring-shaped wave washer having a longitudinally undulating circumferential extent forming a circular hoop interrupted by a radial slot.

4. The device as set forth in claim 1, wherein the at least one wave washer comprises a spiral-shaped wave washer, the spiral-shaped wave washer having a longitudinally undulating extent tat sweeps through an angle greater than 360 degrees, such that the extent spirals inwardly from relatively larger-diameter outer ring portions to increasingly relatively smaller-diameter inner ring portions, the outer and inner ring pardons undulating in the same laterally extending plane.

5. The device as set forth in claim 1, further comprising a flexible circumferential skirt disposed about and between lateral perimeters of the first and second plate members, therein defining an interior volume of the device in which the at least one wave washer is disposed.

6. The device as set forth in claim 5, wherein the flexible circumferential skirt comprises a resilient material.

7. The device as set forth in claim 5, wherein the flexible circumferential skirt is porous.

8. The device as set forth in claim 1, wherein the at least one wave washer comprises multiple wave washers.

9. The device as set forth in claim 8, wherein the multiple wave washers comprise a plurality of concentric wave washers.

10. The device as set forth in claim 1, wherein at least one of the first and second plates includes a wave washer securing mechanism mounted to the inner surface thereof.

11. An intervertebral spacer device comprising
   first and second plates, the plates being disposed in a spaced apart relationship such that one plate surface of the first plate faces one plate surface of the second plate, the facing surfaces being inner surfaces, and alternative faces of each plate being outer surfaces; and
   at least one restoring force providing element disposed between the inner surfaces of the first and second plates, and disposed such that a compressive load applied to the outer surfaces of the plates is counteracted by at least one spiral-shaped wave washer, the the spiral-shaped wave washer having a longitudinally undulating extent that sweeps through an angle greater than 360 degrees, such that the extent spirals inwardly from relatively larger-diameter outer ring portions to increasingly relatively smaller-diameter inner ring portions, the outer and inner ring portions undulating in the same laterally extending plane.

12. The device as set forth in claim 11, further comprising a flexible circumferential skirt disposed about and between lateral perimeters of the first and second plates, therein defining an interior volume of the device in which the at least one spiral-shaped wave washer is disposed.

13. The device as set forth in claim 12, wherein the flexible circumferential skirt comprises a resilient material.

14. The device as set forth in claim 12, wherein the flexible circumferential skirt is porous.

15. The device as set forth in claim 11, wherein at least one of the first and second plates includes a wave washer securing mechanism mounted to the inner surface thereof.

16. An intervertebral spacer device comprising:
   first and second plates, the plates being disposed in a spaced apart relationship such that one plate surface of the first plate faces one plate surface of the second plate, the facing surfaces being inner surfaces, and the alternative faces of each plate being outer surfaces; and
   at least one ring-shaped wave washer disposed between the inner surfaces of the first and second plates, and disposed such that & compressive load applied to the outer surfaces of the plates is counteracted by the ring-shaped wave washer, the ring-shaped wave washer having a longitudinally undulating circumferential extent forming an uninterrupted circular hoop.

17. The device as set forth in claim 16, wherein the ring-shaped wave washer further includes a radial slot.

18. The device as set forth in claim 16, further comprising a flexible circumferential skirt disposed about and between lateral perimeters of the first and second plates, therein defining an interior volume of the device in which the at least one ring-shaped wave washer is disposed.

19. The device as set forth in claim 18, wherein the flexible circumferential skirt comprises a resilient material.

\* \* \* \* \*

UNITED STATES PATENT AND TRADEMARK OFFICE
CERTIFICATE OF CORRECTION

PATENT NO.    : 6,758,861 B2
DATED         : July 6, 2004
INVENTOR(S)   : James D. Ralph, Stephen Tatar and Joseph P. Errico It is certified that error appears in the above-identified patent and that said Letters Patent is hereby corrected as shown below:

Column 8,
Line 39, "toast" should read -- least --.
Line 51, "art" should read -- an --.
Line 61, "tat" should read -- that --.
Line 65, "pardons" should read -- portions --.

Column 10,
Line 20, "&" should read -- a --.

Signed and Sealed this

Twenty-eighth Day of December, 2004

JON W. DUDAS
*Director of the United States Patent and Trademark Office*